US006653063B2

(12) United States Patent
Carver et al.

(10) Patent No.: US 6,653,063 B2
(45) Date of Patent: Nov. 25, 2003

(54) HEMATOLOGY COMPOSITION USING PRESERVED WHITE BLOOD CELLS IN COMBINATION WITH SOURCE PARTICLES TO SIMULATE NATIVE WHITE BLOOD CELLS AND METHOD OF MAKING SAME

(75) Inventors: Frank J. Carver, Marco Island, FL (US); James D. Lapicola, Pleasant Hill, CA (US)

(73) Assignee: Hematronix, Inc., Plano, TX (US)

( * ) Notice: Subject to any disclaimer, the term of this patent is extended or adjusted under 35 U.S.C. 154(b) by 268 days.

(21) Appl. No.: 09/877,709

(22) Filed: Jun. 8, 2001

(65) Prior Publication Data

US 2002/0022269 A1 Feb. 21, 2002

Related U.S. Application Data

(60) Provisional application No. 60/210,918, filed on Jun. 12, 2000.

(51) Int. Cl.[7] .................................................. A61K 35/78
(52) U.S. Cl. .......................... 435/2; 424/532; 424/533; 424/534; 424/725; 424/778
(58) Field of Search ............................. 435/2; 424/532, 424/533, 534, 725, 778

(56) References Cited

U.S. PATENT DOCUMENTS

| 3,873,467 A | 3/1975 | Hunt |
| 3,977,995 A | 8/1976 | Louderback et al. |
| 4,704,364 A | 11/1987 | Carver et al. |
| 4,791,355 A | 12/1988 | Coulter et al. |
| 5,380,644 A | 1/1995 | Yonkoski et al. |
| 5,512,485 A | 4/1996 | Young et al. |
| 5,672,474 A | 9/1997 | Ryan |
| 5,858,790 A | 1/1999 | Kim et al. |
| 5,902,584 A | 5/1999 | Nicholson et al. |
| 6,146,901 A | 11/2000 | Carver et al. |

Primary Examiner—Jean C. Witz
(74) Attorney, Agent, or Firm—J. David Wharton; Stinson Morrison Hecker LLP

(57) ABSTRACT

A hematology control composition and method of making the composition is provided. The control employs a plurality of components including a synthetic plasma component, a red blood cell component, a platelet component and a leukocyte component. The leukocyte component includes at least one subpopulation having particles derived from other than white blood cells.

6 Claims, No Drawings

HEMATOLOGY COMPOSITION USING PRESERVED WHITE BLOOD CELLS IN COMBINATION WITH SOURCE PARTICLES TO SIMULATE NATIVE WHITE BLOOD CELLS AND METHOD OF MAKING SAME

CROSS-REFERENCE TO RELATED APPLICATIONS

The present application is related to and claims priority from U.S. Provisional Patent Application No. 60/210,918, filed Jun. 12, 2000 and entitled "Composition Using Preserved Animal White Blood Cells Combined With Animal and Non-Animal Source Particles to Simulate Animal White Blood Cells and Method of Making Same" and is related to, claims priority from, and is a continuation-in-part of co-pending application Ser. No. 09/816,911, filed Mar. 23, 2001, and entitled "Hematology Blood Control and Method for Preparation of Same."

STATEMENT REGARDING FEDERALLY SPONSORED RESEARCH OR DEVELOPMENT

Not Applicable.

BACKGROUND OF THE INVENTION

This invention generally relates to the field of hematology. More particularly, this invention relates to a hematology control composition made from a unique combination of elements which simulates vertebrate white blood cells. Further, the present invention relates to a method of making such a hematology control composition.

Instrumentation useful in analyzing blood components and chemistry has been used for many years. Over time, the accuracy and sensitivity of such hematology instruments have steadily advanced. Early hematology instrumentation has evolved into relatively complex machinery which analyzes the discrete components of blood based upon the intricate and subtle characteristics of its components. The most recently developed automated hematology instrumentation is capable not only of detecting red blood cells and platelets, but also is capable of conducting a multi-part analysis of human white blood cells.

Methods for analyzing blood cells involve an examination of both the electrical and optical properties the cell. For instance, the Beckman-Coulter™ five-part white blood cell analysis instrument utilizes three different technologies for blood cell analysis. These technologies include electrical impedance, a DC mathematical manipulation commonly referred to as conductance, and laser technology. Instruments made by other manufacturers, such as Abbott Diagnostics™, Technicon™, and TOA™, also use electrical impedance, DC conductance and/or laser technology, individually or in combination.

Although the basic types of electronic technology utilized may appear similar or identical among machinery made by different manufacturers, each manufacturer has a unique implementation for the instrument hardware and software that is required to analyze blood cells. The individual implementation of these technologies by various manufacturers has resulted in a wide array of reagents and methodologies, each one specific to a particular instrument of a particular manufacturer. Accordingly the complexity and expense associated with the use of such hematology instrumentation can be significant. There is no single reagent and no single methodology which may be used with a plurality of instruments.

In order to ensure that a particular hematology instrument is working properly, governments have mandated that there be a method to verify the integrity of the instrument using a blood control composition. To provide accurate data, a control composition should contain components which represent each of the cellular elements of fresh blood, as well as a liquid component to serve as a suspending media, a function similar to that performed by human plasma. This synthetic plasma usually contains components that are identical or similar to, or function identical to or similar to, native plasma. To achieve this end, the components of synthetic plasma include inorganic salts, organic and/or inorganic buffers, and a viscous material for maintaining homeostasis which is similar to native plasma proteins. Additionally, the control composition should have a shelf life that is sufficient for the composition to be used for days, weeks, or months while the consistency of instrument performance is preserved over time.

Methods for preparing hematology control compositions are dependent upon the hardware and software design of the specific instrument with which the control is to be used, as well as the requirement for extended shelf life. Particles in blood control compositions that behave like human white blood cells, red blood cells, or platelets on a Coulter™ type instrument may not accordingly behave on other instruments, such as instruments manufactured by Abbott Laboratories™, Technicon™, or TOA™. Moreover, because particles in blood control compositions usually are modified forms of various types of blood cells, they often do not behave like living native fresh blood cells. As a result, human white blood cells fixed with a cross-linking agent such as glutaraldehyde may behave like a neutrophil on an Abbott™ instrument, but behave like cellular debris on a Coulter™ instrument. Similarly, specially treated and cross-linked red blood cells from non-mammalian vertebrates may look like mononuclear cells on one type of hematology instrument and look like lymphocytes on another.

Accordingly, there remains a need in the hematology instrumentation industry for a hematology control composition which functions as a leukocyte subpopulation analogue and contains one or more non-cellular components. Such non-cellular components exhibit enhanced viability and shelf-life. Prior to the present invention, non-cellular components and cellular components have not been used in combination with treated native white cell components for use as white blood cell subpopulations in a blood control for 5-part white blood cell analyzers.

SUMMARY OF THE INVENTION

Accordingly, in one of its aspects, the present invention provides a hematology control composition having at least one non-animal component which functions as a leukocyte analogue for at least one subpopulation of leukocytes.

In another of its aspects, the present invention provides a hematology control composition having at least one non-animal component which functions as a leukocyte analogue for a plurality of subpopulations of leukocytes.

In yet another aspect, the present invention provides a hematology control composition having at least one non-animal component which function as a leukocyte analogue for at least one subpopulation of leukocytes, wherein the control composition may be made more easily and less expensively than prior art control compositions.

In an additional aspect, the present invention provides a method of making a hematology control composition having the qualities disclosed herein.

According to the present invention, the foregoing and other aspects are achieved by a hematology control composition having a plurality of components including a synthetic plasma component, a red blood cell component, a platelet component and a leukocyte component. The leukocyte component includes at least one subpopulation having particles derived from other than white blood cells.

Additional aspects of the present invention are achieved by a method of making a hematology control composition. The method of the present invention includes providing a synthetic plasma solution, adding a human red blood cell component to the plasma solution, adding a sufficient volume of surrogate or real platelets to the plasma solution and adding a volume of particles representing a plurality of human white blood cell subpopulations. At least one of the white blood cell subpopulations includes particles from other than white blood cells.

DETAILED DESCRIPTION OF THE INVENTION

The present invention is directed to a white blood cell control composition which simulates animal white blood cells and is made from a unique combination of components. The present invention further is directed to a method of making the novel white blood cell control composition of the present invention. The particular embodiments and methods described herein are intended in all respects to be illustrative rather than restrictive. Alternative embodiments will become apparent to those skilled in the art to which the present invention pertains without departing from its scope.

Preserved or aldehyde-fixed native white blood cell preparations include the true white cell type(s), such as a preserved neutrophil that is displayed on an instrument as a neutrophil, and simulating a cell type, such as a preserved white cell that looks like a neutrophil on an Abbott Model 3500 but looks like cellular debris or platelet aggregates on a Coulter Model MAXM instrument.

Simulated white blood cells from fixed red blood cells or commercially prepared micro beads may be produced by a number of methods. Fixed red blood cells are described in U.S. Pat. Nos. 5,380,644, 4,704,364 and 3,873,467. Micro beads are divided into non-biological and biological organic particles. Non-biological organic particles may be commercially prepared from base materials such as polystyrene, polyvinyltoluene, and styrenedivinylbenzene. The use of a single non-biological particle in a blood control is described in U.S. Pat. No. 3,977,995. Commercially prepared micro beads are also defined as those particles with a biological origin as plant pollen. All commercially prepared microbeads will be hereafter referred to as "organic particles".

The methods of preserving vertebrate white cells for simulated or non-simulated white cells include those in a series of patents including U.S. Pat. Nos. 5,672,474 and 5,858,790. Processes and methods for simulating white blood cells from non-white blood cells including organic particles, as can be seen in U.S. Pat. Nos. 3,977,995, 5,380,644, 4,704,364.

The control composition of the present invention utilizes white blood cells to correctly represent (non-simulate) as well as simulate human white blood cell populations. The control composition of the present invention also utilizes non-white blood cell particles to simulate human white blood cell subpopulations. It is well-known that human blood includes five subpopulations of leukocytes. In accordance with the present invention, at least one of the five subpopulations of leukocytes is simulated by non-white blood cell sources. These non-white blood cell particles include latex beads, plant pollen, fixed red blood cells or other particles exhibiting the size and other characteristics of the subpopulation to be simulated. While latex beads, plant pollen and fixed red blood cells are disclosed as non-white cell particles, it is to be understood that other particles also may work as leukocyte subpopulation analogs. Depending on the instrument upon which the control composition is to be used and the desired application to be achieved, various combinations of non-white blood cell particles and white blood cell particles can be utilized in the control of the present invention to achieve a blood control which simulates human blood.

In one application, the control composition may include latex beads or plant pollen to represent vertebrate lymphocytes, monocytes and granulocytes. The control may also utilize cross-linked white blood cells to represent other leukocyte subpopulations. A synthetic plasma replacement is also used and human red blood cells function as the human red blood cells of the blood. Preserved red blood cells to simulate vertebrate platelets. The overall control product, therefore, closely simulates substantially all components of human blood.

The present invention is designed for use on a multi-part blood analyzer, although it also is envisioned for use on other blood analyzers. For a multi-part white blood cell analyzer, latex beads may be used to provide the lymphocyte subpopulation and the mononuclear subpopulation, depending on the size of the beads to be used. It is to be understood that latex beads can be sized to achieve the desired simulated subpopulation as the instrument and circumstances may dictate.

The method for making the control composition of the present invention includes adding the red blood cell component and a synthetic plasma replacement into a sterile bottle. A sufficient volume of surrogate platelets are then added. The white blood cell components for the subpopulations of the control are then added to the mixture. The resulting control can then be preserved for later use.

The following are examples of combinations of components that may be used to prepare white blood cell control compositions in accordance with the present invention as well as methods for making the control compositions. It will be understood and appreciated that these examples are in no way intended to limit the scope of the present invention but are merely offered by way of illustration.

EXAMPLE I

The following is an example of a white blood cell blood control composition, and method of making thereof, which comprises organic particles in combination with vertebrate white blood cells. The product resulting from this example is intended for use with hematology instrumentation utilizing only impedance technology to measure two or more white blood cell populations.

The following materials were utilized in the preparation of this particular blood control composition: Organic based commercially available particles (e.g. latex beads) or particles of a biological origin (e.g. plant pollen) having a size of about 4 $\mu$ to about 20 $\mu$ to represent vertebrate white blood cells (e.g. lymphocytes, monocytes, and granulocytes); cross-linked vertebrate white blood cells to represent vertebrate white cells (e.g. lymphocytes, monocytes, and granulocytes); synthetic plasma replacement; preserved human red blood cells for use as red blood cells; preserved blood cells in a synthetic plasma; and preserved blood cells (e.g. goat) to simulate vertebrate platelets.

Each component of the resultant composition was prepared as follows: 100 mL of human red blood cells in a synthetic plasma replacement, at a count of 0.5 to 8 $10^6/\mu L$, was added to a sterile 200 mL container. A sufficient volume of surrogate platelets to obtain a count of 5 to $1,000\times10^3/\mu L$ was then added to the container containing the red blood cell component. A volume of particles to obtain a count of 1 to $99\times10^3/\mu L$ was subsequently added to the container using the following components: a sufficient volume of organic based commercially available particles (e.g. latex beads) as supplied to give a lymphocyte population equal to 1 to 99 percent of the total 100% of the white blood cell population, a sufficient volume of organic based commercially available particles (e.g. latex beads) is added to give a mononuclear population of 1 to 99 percent of the total 100% of the white blood cell population or a percentage minus that from the lymphocyte population, then a sufficient volume of cross-linked vertebrate white blood cells was added to represent granulocytes that are 1 to 99 percent of the total 100% of the white blood cell population or a percentage minus that of the preceding lymphocyte and monocyte populations.

EXAMPLE II

Fixed red blood cells and vertebrate white cells to be used in a blood control product for use on impedance technology only hematology instruments to measure two or more white cell populations. The following components were used: cross-linked vertebrate red blood cells with sufficient volume to represent a single type of vertebrate white blood cells (e.g. lymphocytes, monocytes, or granulocytes), cross-linked vertebrate white blood cell to represent one or more type of vertebrate white cells (e.g. lymphocytes, monocytes, and granulocytes), synthetic plasma replacement, preserved human red blood cells for use as red blood cells, preserved blood cells in a synthetic plasma, and preserved blood cells (e.g. goat) to simulate vertebrate platelets.

The sample formulation for Example 2 was prepared as follows: 100 mL human red blood cells in a synthetic plasma replacement, at a count of 0.5 to $8\times10^6/\mu L$, was added to a sterile 200 mL bottle, a sufficient volume of surrogate platelets to obtain a count of 5 to $1,000\times10^3/\mu L$ was then added, a volume of particles to obtain a count of 1 to $99\times10^3/\mu L$ was added, the particles using the following components: a sufficient volume of cross-linked vertebrate red blood cells to give a lymphocyte population equal to 1 to 99 percent of the total 100% of the white blood cell population, a sufficient volume of cross-linked vertebrate white blood cells to represent granulocytes or alternatively the neutrophil population of 1 to 99 percent of the total 100% of the white blood cell population and also containing a lesser percentage of native lymphocytes and/or mononuclear type cells or a percentage minus that of the preceding lymphocyte or monocyte populations.

EXAMPLE III

Organic particles with vertebrate white cells to be used in a blood control product for use on impedance, laser, and/or opacity technology hematology instruments to measure 2 or more white cell populations. The following materials were used: Latex beads or particles of a biological origin of a size to represent vertebrate white blood cells (e.g. eosinophils), cross-linked vertebrate white blood cells to represent vertebrate white cells (e.g. lymphocytes, monocytes, basophils, neutrophils, and eosinophils), synthetic plasma replacement, preserved human red blood cells for use as red blood cells, preserved blood cells in a synthetic plasma, preserved blood cells (e.g. goat) to simulate vertebrate platelets.

The sample formulation for Example 3 was made as follows; 100 mL human red blood cells in a synthetic plasma replacement, at a count of 0.5 to $8\times10^6/\mu L$, was added to a sterile 200 mL bottle, a sufficient volume of surrogate platelets to obtain a count of 5 to $1,000\times10^3/\mu L$ was then added, a volume of particles to obtain a count of 1 to $99\times10^3/\mu L$ was added, the particles having the following components: a sufficient volume of organic based commercially available particles (e.g. latex beads) to give a lymphocyte population equal to 1 to 99 percent of the total 100% of the white blood cell population minus the mononuclear, eosinophil, neutrophil and basophil populations, a sufficient volume of organic based commercially available particles (e.g. latex beads) to give a mononuclear population of 1 to 99 percent of the total 100% of the white blood cell population or a percentage minus that from the lymphocyte, eosinophil, neutrophil and basophil populations, a sufficient volume of cross-linked vertebrate white blood cells to represent monocytes to replace the above organic based mononuclear population of 1 to 99 percent of the total 100% of the white blood cell population or a percentage minus that from the lymphocyte, eosinophil, and neutrophil populations, a sufficient volume of particles of a biological original (e.g. plant pollen) to give an eosinophil population of 1 to 99 percent of the total 100% of the white blood cell population or a percentage minus that from the lymphocyte, mononuclear, neutrophil, and basophil populations, a sufficient volume of cross-linked vertebrate white blood cells to represent the neutrophil population of 1 to 99 percent of the total 100% of the white blood cell population or a percentage minus that of the lymphocyte, monocyte, basophil, and eosinophil populations.

EXAMPLE IV

Fixed red blood cells and vertebrate white cells to be used in a blood control product for use on impedance, laser, and/or opacity technology hematology instruments to measure two or more white cell populations. The following materials were used: one or more cross-linked vertebrate red blood cells with sufficient volume to represent vertebrate white blood cells (e.g. lymphocytes, monocyte, basophils, neutrophils, and eosinophils), cross-linked vertebrate white blood cells to represent vertebrate white cells (e.g. lymphocytes, monocytes, basophils, neutrophils, and eosinophils), synthetic plasma replacement, preserved human red blood cells for use as red blood cells, preserved blood cells in a synthetic plasma, preserved blood cells (e.g. goat) to simulate vertebrate platelets.

The sample formulation for Example 4 was prepared as follows: 100 mL human red blood cells in a synthetic plasma replacement, at a count of 0.5 to $8\times10^6/\mu L$, was added to a sterile 200 mL bottle, a sufficient volume of surrogate platelets to obtain a count of 5 to $1,000\times^3/\mu L$ was added, a volume of particles to obtain a count of 1 to $99\times^3/\mu L$ was then added, the particles having the following components: a sufficient volume of cross-linked vertebrate red blood cells to give a lymphocyte population equal to 1 to 99 percent of the total 100% of the white blood cell population, a sufficient volume of cross-linked vertebrate red blood cells to give a mononuclear population of 1 to 99 percent of the total 10% of the white blood cell population or a percentage minus that from the lymphocyte, basophil, eosinophil and neutrophil populations (this may be done for instrument technologies similar to the TOA NE-8000 but not for the Coulter 5-part instruments due to patent restrictions, a sufficient volume of particles of a biological origin (e.g. plant pollen) to give an eosinophil population of 1 to 99 percent of the total 100% of the white blood cell population or a percentage minus that from the lymphocyte, monocyte, basophil, and neutrophil populations, a sufficient volume of cross-linked vertebrate white blood cells to represent the neutrophil population of 1 to 99 percent of the total 100% of the white blood cell population or a percentage minus that of the lymphocyte, monocyte, basophil, and eosinophil populations.

EXAMPLE V

The bulk Production of Source Leukocytes was achieved using the following materials: Glutaraldehyde Lot# 20509 (KOH neutralized on May 10, 2000), Lot # SAP-008 Stock solution of Saponin Lot# 1190, Part# 01c. 0080 (R&D), Lot # SAP-008; prepared on Apr. 14, 2000), 100 mL saponin suspended in 1 Liter 50% M—Ringers solution. Mix with stirring bar overnight. (NOTE: The storage container for saponin was shaken prior to removing the sample), diluted to 4 Liters for a final 25 mL saponin/L of 50% M-Ringers, bottle labeled as Stock Solution, working Solution; 40 mL stock diluted to 1000 mL with Aquasol®, M-Ringers, Lot# 023, Quench Lot# R&D-Q004 prepared on Apr. 19, 2000; Neutral Quench Formula, 8.0 g/L NaCl, 46.0 g/L $Na^2SO^4$, pH=9.08, Osmolarity=972, Source Leukocytes from Central Blood Center (drawn May 9, 2000 (1 day old) stored in the shipping container until use, Fluid-4 RBC's, Lot# C8472, ISO-W Lot# 175, 1L centrifuge bottles, 50 mL disposable centrifuge tubes, Secondary Fix consisting of 1% glutaraldehyde in 50% ISO-W equilibrated at room temperature prepared fresh, The following methods were used:
Full Unit Method:

The source leukocyte cells were removed from the Styrofoam cooler, mixed, and 40 mL poured directly from a transfusion bag into a pre-water rinsed 50 mL centrifuge tube. The samples were assayed on the Counter MAXM in R&D using newly formulated Hematronix Diff reagents (Lot# 2032) with a final blended pH=4.6, the contents of a tube (40 mL) was poured into a 1L bottle, 400 mL lyse was added to the first 1L bottle and incubated for 2 minutes at room temperature. The sample was mixed by gentle swirling. The lysed cells were then poured into a clean 1L bottle containing 50 mL quench and 1 mL glutaraldehyde. The cells were poured back into the original 1L container, then back, then finally in the original container. The sample was shaken for about 30 seconds after quench and before the 1 hour fix at room temperature. 400 mL lyse was added to the second bottle 30 seconds after the first bottle and stopped 2 minutes later by dumping the lysed cells into the quench/glutaraldehyde which was previously added to a separate clean 1L bottle. Mixing was the same as the first bottle. A second set of two bottles was prepared as above and all bottles were incubated as above (i.e. 1 hour at room temperature). All four bottles were centrifuged for 4 minutes at 2,000 RPM. The supernatant was removed and replaced with 500 mL room temperature equilibrated Secondary Fix (50% ISO-W with 1% glutaraldehyde). Samples were mixed for about 30 seconds to resuspend the particles and to insure complete mixing. All bottles were placed in a water bath at 37° C. for 60 minutes. The 1L containers were removed from the water bath and all samples cooled and fixed at room temperature.

In summary, the present invention is directed to a white blood cell control composition which simulates animal white blood cells and is made from a unique combination of components. The present invention further is directed to a method of making the novel white blood cell control composition of the present invention. The present invention has been described in relation to particular embodiments which are intended in all respects to be illustrative rather than restrictive. Alternative embodiments will become apparent to those skilled in the art to which the present invention pertains without departing from its scope.

From the foregoing, it will be seen that this invention is one well adapted to attain all the ends and objets hereinabove set forth together with other advantages which are obvious and which are inherent to the composition and method. It will be understood that certain features and subcombinations are of utility and may be employed without reference to other features and subcombinations. This is contemplated by and is within the scope of the claims.

Having thus described the invention, what is claimed is:

1. A hematology control composition, said composition comprising:

a synthetic plasma solution;

a red cell component;

a platelet component; and a plurality of leukocyte components, wherein said leukocyte components include at least one subpopulation comprising non-white blood cell particles, and at least one subpopulation comprising white blood cell particles.

2. The composition of claim 1 wherein the non-white blood cell particles include latex beads.

3. The composition of claim 2 wherein the non-white blood particles include pollen.

4. The composition of claim 3 wherein the platelet component comprises simulated platelets.

5. The composition of claim 4 wherein the simulated platelets comprise preserved red blood cells.

6. A method of making a hematology control, said method comprising the steps of:

providing a synthetic plasma solution;

adding a human red blood cell component to said plasma solution;

adding a sufficient volume of surrogate platelets to said plasma solution; and adding a volume of particles representing a plurality of human white blood cell subpopulations, wherein at least one subpopulation comprises non-white blood cell particles, and at least one subpopulation comprises white blood cell particles.

* * * * *

UNITED STATES PATENT AND TRADEMARK OFFICE
CERTIFICATE OF CORRECTION

PATENT NO. : 6,653,063 B2
DATED : November 25, 2003
INVENTOR(S) : Frank J. Carver and James D. Lapicola It is certified that error appears in the above-identified patent and that said Letters Patent is hereby corrected as shown below:

Title page,
Item [60], Related U.S. Application Data, insert -- and co-pending application No. 09/816,911 filed March 23, 2001." after "Provisional application No. 60/210,918, filed on Jun. 12, 2000."

Signed and Sealed this

Fourth Day of May, 2004

JON W. DUDAS
*Acting Director of the United States Patent and Trademark Office*